US006957227B2

(12) United States Patent
Fogel et al.

(10) Patent No.: US 6,957,227 B2
(45) Date of Patent: *Oct. 18, 2005

(54) AUTOMATED DATA INTEGRITY AUDITING SYSTEM

(75) Inventors: Barry S. Fogel, Brookline, MA (US); A. James Kazmer, Andover, MA (US); Steven B. Littlehale, Jamaica Plain, MA (US)

(73) Assignee: LTCQ, Inc., Lexington, MA (US)

( * ) Notice: Subject to any disclaimer, the term of this patent is extended or adjusted under 35 U.S.C. 154(b) by 221 days.

This patent is subject to a terminal disclaimer.

(21) Appl. No.: 10/353,394

(22) Filed: Jan. 29, 2003

(65) Prior Publication Data

US 2003/0115195 A1 Jun. 19, 2003

Related U.S. Application Data

(63) Continuation of application No. 09/519,683, filed on Mar. 7, 2000, now Pat. No. 6,542,905.
(60) Provisional application No. 60/123,736, filed on Mar. 10, 1999.

(51) Int. Cl.$^7$ ............................................. G06F 17/30
(52) U.S. Cl. ..................................... 707/102; 707/200
(58) Field of Search ............................... 707/6, 8, 100, 707/102, 200, 202; 705/1, 2, 14, 62; 706/52; 712/32; 710/19; 714/1, 15, 25; 725/48

(56) References Cited

U.S. PATENT DOCUMENTS

| 4,470,116 | A | | 9/1984 | Ratchford | 701/35 |
|---|---|---|---|---|---|
| 5,359,509 | A | | 10/1994 | Little et al. | 705/2 |
| 5,404,509 | A | | 4/1995 | Klein | 707/101 |
| 5,469,563 | A | | 11/1995 | Morita | 714/25 |
| 5,576,755 | A | * | 11/1996 | Davis et al. | 725/48 |
| 5,715,180 | A | | 2/1998 | Hu | 702/108 |
| 5,717,607 | A | | 2/1998 | Hu | 702/123 |
| 5,745,896 | A | | 4/1998 | Vijaykumar | 707/100 |
| 5,765,172 | A | | 6/1998 | Fox | 707/204 |
| 5,778,066 | A | * | 7/1998 | Shah et al. | 705/62 |
| 5,784,635 | A | * | 7/1998 | McCallum | 712/32 |
| 5,845,285 | A | | 12/1998 | Klein | 707/101 |
| 6,082,776 | A | | 7/2000 | Feinberg | 283/72 |
| 6,526,396 | B1 | * | 2/2003 | Hiratsuka et al. | 706/52 |
| 6,542,905 | B1 | * | 4/2003 | Fogel et al. | 707/200 |

* cited by examiner

Primary Examiner—Apu Mofiz
(74) Attorney, Agent, or Firm—Lipsitz & McAllister, LLC (57) ABSTRACT

An automated computer-based data integrity auditing system is provided for use in the healthcare industry, financial industry, academic and educational fields, or any other field in which a need exists for monitoring data integrity. Coded data received from a service organization are checked for proper coding and completeness. The coded data are stored in a computer database together with indicators specifying bad data found during the checking step. At least one data integrity test is applied to a portion of the data which does not have any bad data specified by an indicator. Any data validity problems located by the data integrity test(s) are identified. Reports may be generated to identify a score assigned to the tested portion of the data, the data validity problems, or suggestions for resolving the data validity problems.

28 Claims, 1 Drawing Sheet

AUTOMATED DATA INTEGRITY AUDITING SYSTEM

BACKGROUND OF THE INVENTION

The present invention relates to an automated computer-based data integrity auditing system. The first embodiment of the invention is a system for auditing patient assessment data produced by nursing homes. It will be evident, however, that the system has utility for any industry that relies upon standardized databases in the production or evaluation of products or services, as long as those databases have logical and practical relationships among items, and/or discrete scales that are internally consistent, and are correlated with others in a predictable way.

When databases are used to produce or evaluate products and services that are essential to the mission of an industry, validity of data is necessary to ensure the quality of products or services. Such industries include, without limitation, healthcare, financial services, and education. The invention is described in a healthcare context. However, it is evident that the methods described are applicable to other industries. The invention is applicable to any industry which utilizes databases having particular relationships between database elements.

In recent years, both the cost and the potential benefits of healthcare have increased substantially. Consumers of care, and payers for care (if they are other than the consumers), increasingly demand proof of benefits or quality of care to justify the funds they spend on that care. To prove the benefits of care and to evaluate the quality of care, it is necessary to measure processes and outcomes of care using standardized methodology. Standardized measurement permits comparisons over time and among care providers, and may allow for risk adjustment.

Standardized assessment of care outcomes and processes requires measurement of patients' health status and recording of the services they receive. When such data are valid, they also may be used for quality improvement efforts. Decision support algorithms can be based upon such data, and performance measures based upon such data can be fed back to quality improvement teams. Additional uses of standardized health status and health services data include: 1) prediction of care outcomes (prognosis); 2) needs assessment for communities or healthcare institutions; 3) regulatory oversight of healthcare providers; and 4) calculation of fees or reimbursements based on illness severity or service intensity.

Nursing homes in the U.S. certified by the Health Care Financing Administration (HCFA) to receive Medicare or Medicaid reimbursement are subject to a requirement to submit standardized assessment data on every one of their residents. The mandatory database is called the Minimum Data Set (MDS). The MDS comprises over 500 items, mainly checklist and multiple-choice items, dealing with the resident's demographics, baseline functioning and preferences, current health status, and recent and present health services used.

Nursing homes seeking Medicare reimbursement for a resident must perform MDS assessment on or about days 5, 14, 30, 60 and 90 of a resident's admission. Nursing homes seeking Medicaid reimbursement must perform MDS assessments by day 14 after a resident is admitted, and quarterly thereafter. A complete, comprehensive MDS must be submitted based on the resident's status on admission, and must be updated annually thereafter. Medicare residents require complete assessments to be done (i.e., updated) at each follow-up. Medicaid residents must have a less-comprehensive MDS assessment quarterly, and a full reassessment every year. Facilities must transmit the required MDS assessments electronically to designated State agencies, using a mandatory format for electronic data interchange.

Medicare reimbursement for skilled nursing care is determined by applying a classification algorithm to one hundred eight of the MDS items. Based on these items, HCFA and its fiscal intermediaries classify a nursing home resident into one of forty-four Resource Utilization Groups (RUGS). Each RUG is associated with a specific rate of per diem reimbursement.

HCFA also has designated quality indicators (QIs) calculated from MDS data. These QIs are rates of various clinical conditions that may be correlated with quality of care. For example, one QI is the rate of pressure ulcers (bed sores). In general, higher rates of pressure ulcers are associated with less satisfactory care. A more accurate assessment of quality adjusts the QI for various factors that influence the risk of pressure ulcers, e.g., malnutrition and immobility. Even more accurate performance measures are based on the incidence rather than the prevalence of pressure ulcers, or on rates of healing of pre-existing pressure ulcers.

Nursing facilities can use MDS data to manage their legal liability for adverse outcomes of care. In some cases, MDS data concerning risk factors enable a facility to show that a person experiencing a poor outcome was at especially high risk for that outcome. This would argue that the care was not necessarily substandard. In others, a facility can show that its overall performance in a given area of care was superior, so that a particular adverse event represented a chance occurrence rather than the result of a pattern of negligence or misconduct. Advocates and attorneys bringing complaints against nursing homes can use MDS data in similar ways with opposite objectives.

The various purposes of the nursing home MDS, or of any other health status/health service database can only be served if the data are valid. This requires valid assessments, accurate coding of the assessments, and accurate representation of the codes in electronic form whether via manual data entry or via scanning of forms. The requirement for validity is extremely high if data on individual residents are to be used for clinical decision-making or legal purposes. If only aggregated data from entire facilities or units will be analyzed, it may only be necessary that validity exceed a reasonable lower bound.

The "gold standard" of validity testing is independent verification of the data found in the electronic MDS record by a qualified expert who directly examines the resident, interviews caregivers, and reviews all relevant clinical records. This is an expensive process, feasible only for a small sample of residents at any given facility. In some cases, the "gold standard" can never be attained because the status of the resident has changed between the time of the computerized MDS assessment and the time of the validation assessment by the expert.

Therefore, there is a need to:
1) define a reasonable proxy measure for the validity of health status/health services databases;
2) define a way to quantify data validity, and to indicate whether particular data elements are trustworthy;
3) determine the acceptability of data for the different purposes to which it may be put;
4) guide assessors and coders in modifying their processes to systematically improve data quality;

5) ensure higher quality data during the process of assessment, coding, and data entry, before submission of the data for analysis, reimbursement, or other uses; and 6) automate the processes of data quality assessment and improvement to make them economical and feasible for universal application.

The present invention provides an advantageous system that meets the aforementioned needs. In particular, the invention defines a proxy measure, called data integrity, for data validity and describes a system for measuring it.

It will be apparent to one skilled in the art that the methodology of the present invention is applicable not only to various kinds of health status/health service data, but to any standardized data concerning service processes and the status of the individuals or objects to which those processes apply. A simple extension is to home care, for which the Outcome and Statistics Information Set (OASIS), a tool similar to the MDS, is used in regulation and reimbursement. In the financial service industry, data validity tests can be applied to databases with data that include customers' demographics, portfolios, transaction histories, preferences, and satisfaction. In education, data validity tests can be applied to databases of demographics, scores on scholastic aptitude and achievement tests, courses taken and scores given, etc. The system for evaluating MDS data integrity described in detail here should therefore be regarded as just one example of a broadly applicable methodology.

SUMMARY OF THE INVENTION

In accordance with the invention, a system is provided for identifying data integrity issues, and showing how they can be either resolved or addressed adequately by ancillary documentation. In the case of healthcare, this would appear in the clinical record. In a financial context, information for addressing integrity issues might appear in footnotes to a financial statement, etc.

The invention also provides a system for identifying the process issues likely to be causing frequently-occurring data integrity issues. Moreover, a system is provided for identifying the impact of data integrity issues on various specific uses of the data, e.g., on the use of MDS data for RUGS-based Medicare reimbursement.

A system is also disclosed for identifying and addressing data integrity issues before the submission of the data for analysis or other uses. Still further, specific tests of data integrity applicable to MDS data are provided.

The invention also provides text, linked to each data integrity test, that explains to the user the likely explanation for the data integrity issue identified, along with suggestions for correcting the assessment or documenting unusual clinical circumstances that would allow the data integrity issue to arise from a valid assessment. Additionally, the invention provides for the use of the data integrity audit system as the basis of a knowledge management network linking nursing homes. The network would be used for the sharing of clinical best practices, for communicating clinical and administrative advice, and for various commercial purposes.

More specifically, the invention describes the implementation of an exemplary system through computer software and a related system for identifying and correcting potential data validity problems prior to data submission. The invention further specifies elements in the implementation of the two related systems via computer software.

The invention also describes and specifies a method for estimating and grading the validity of quantitative and categorical data submitted electronically by a healthcare provider or other service organization. The estimate, or proxy measure, is referred to herein as data integrity. Applied prospectively, the method can be used to ensure the integrity of data before their submission for a clinical, financial, or regulatory purpose. The prospective data integrity audit can be used as the raison d'être of a network of care providers. Because the network administrator would have available detailed and reliable clinical information on every resident of every facility in the network, the network could be an especially effective tool for targeting messages to management, supporting clinical decision-making, and aggregating the networked facilities' demand for supplies and services. Better purchase terms and more efficient supply chain management would result.

In accordance with the invention, a method is provided for evaluating and scoring the integrity of data provided by an organization, such as a nursing home, in which coded data is received from the organization. The received data is checked for proper coding and completeness. The coded data are then stored in a computer database together with indicators specifying 'bad' (i.e. miscoded or otherwise unusable) data found during the checking step. The stored coded data are then processed in a computer to apply one or more data integrity tests to that portion of data stored in the database that does not have any indicators of bad data. A score is assigned to the portion of data based on the data integrity test, and a report is generated that identifies the score together with suggestions for resolving any data validity problems suggested by the data integrity test.

A method is also provided for calculating the potential impact of data integrity problems on reimbursement, such as Medicare or Medicaid reimbursement, where the reimbursement for each individual is based on a vector of items from a single assessment. In particular, for each individual assessment and each data integrity issue involving reimbursement-related items, a determination is made as to how that data integrity issue could be resolved by revising a single item response. The smallest such change in favor of the payer is determined that would resolve each data integrity issue of an individual assessment. Data integrity issues are resolved in the order that they are listed in the audit system. The process is repeated as necessary until no data integrity issues remain in the amended data vector. This amended data vector favors the payer. A similar process is applied to produce an amended data vector that favors the care provider. Reimbursement is calculated under three hypothetical conditions: that the original data vector is valid; that the first amended data vector is valid; and that the second amended data vector is valid.

A computer program is disclosed for assisting facilities in the completion and submission of required regulatory data. The computer program comprises a routine for checking data provided by the facility for proper coding and completeness in accordance with regulatory requirements. The program also includes a routine for appending indicators to the data. The indicators specify bad data found during the checking step. The data are processed in accordance with the computer program to apply one or more data integrity tests to a portion of the data that does not have any indicators of bad data. The program assigns a score-to the portion of data based on the data integrity test. A report is then generated that identifies the score together with suggestions for resolving any data validity problems located during the data integrity test. The report can be provided to the facility on a real-time basis. In this manner, the facility is able to immediately revise the data in response to the real-time report prior to submission to the regulatory facility.

DETAILED DESCRIPTION OF THE INVENTION

Figure 1:
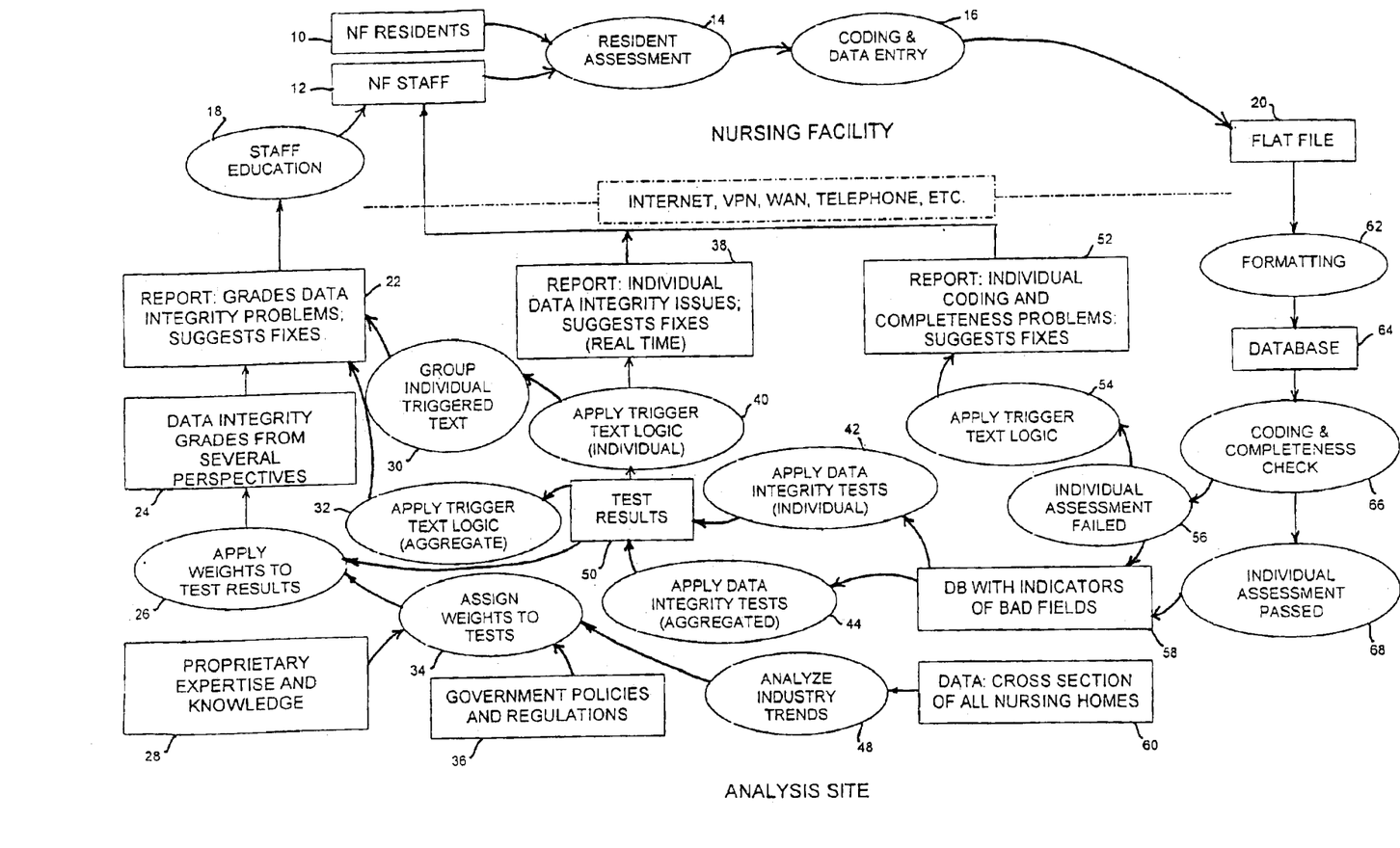
The FIGURE is a flow chart representing an implementation of the invention in the healthcare field, in which the integrity of nursing facility data is audited.

The present invention is concerned with data integrity, and more particularly the auditing of data to ensure that a given set of data is valid. Data integrity refers to characteristics of a database that either:

1) should be true most or all of the time if the data arise solely from accurate and properly coded assessments, or;

2) would require independent documentation of some kind in order for the data to be viewed as valid. In this latter case, data integrity entails that the necessary documentation is in fact present.

In discussing data integrity, the term "item" is used with either of two meanings—the correct one will be clear from context.: "Item" either means a variable within a database (e.g., a specific question on a questionnaire), or to the specific value of that variable in a given case (e.g., the code for the subject's answer). Strictly speaking, the latter is an "item response".

Healthcare databases contain data about individuals. When these individuals are recipients of medical services, they are referred to as "patients." When they reside in a nursing home, they are referred to as "residents." The terms "resident" and "patient" may be used interchangeably herein, with the choice dependent upon the context. Although the invention is described by referring to individuals as "patients," in the broadest application of the methodology individuals may be "clients," "customers," "consumers," etc.

Data integrity issues are patterns of items (i.e., item responses) within a database that either could not be the result of an accurate and correctly coded assessment; or i) are unlikely to arise from an accurate and correctly coded assessment, but could arise only under unusual circumstances, or in a specialized clinical population. In either case specific documentation in the clinical record would be required if the data were to be viewed as valid.

Data validity problems are data integrity issues which either:

i) could never be the result of an accurate and correctly coded assessment ii) would require documentation to establish their validity; but lack the necessary documentation;

iii) have been proved to be data validity problems by an independent expert assessment of the resident or group of residents in question.

Data integrity for an individual assessment is based on relationships among item responses for the same assessment of the same patient. It requires that A1) For items being analyzed, there are no missing data.

A2) All coding rules are followed, and no values are out of range.

A3) The recorded dates for admission, assessment, and form completion are in accord with official deadlines.

A4) Item responses are logically consistent with one another. For example, if "none of the above" is scored positive, then none of the items referred to are scored positive.

A5) Item responses are clinically reasonable. For example, a patient in a coma is not scored as independent in daily activities.

A6) Symptoms, conditions, diagnoses, and treatments are in accord with one another, e.g., a patient receiving dialysis has renal failure, a patient with Alzheimer's disease has memory loss or impaired decision making, a patient receiving speech therapy has communication or swallowing problems.

Conditions (A1) through (A4) should always be true; an assessment in which any one of them is not true has a data validity problem. If either of conditions (A5) and (A6) does not hold, there is a data integrity issue. That data integrity issue is a data validity problem when the necessary documentation is absent, or when the necessary documentation is present, but independent expert assessment shows both the documentation and the MDS to be invalid.

Data integrity for a set of assessments from a single care provider over a fixed time interval requires data integrity for each individual patient assessment according to conditions (A1) through (A4), and B1) The proportion of exceptions to conditions (A5) or (A6) above does not exceed an upper confidence limit established using data from a reference set of care providers with data of known or presumed validity.

B2) The rates of specific item responses do not exceed confidence limits established using data from a reference set of care providers with data of known or presumed validity.

B3) Sets of items measuring the same construct (e.g. depression, impaired walking) have internal consistency statistics (e.g. Cronbach's alpha) that exceed a threshold established using data from a reference set of providers with data of known or presumed validity.

B4) Various scales measuring different clinical constructs show expected correlations with one another; i.e. their correlation coefficients or covariances exceed a threshold established from reference data of known or presumed validity. For example, in nursing home residents, cognitive problems and behavioral problems are correlated. A facility in which cognitive problems and behavioral problems were uncorrelated would have a data integrity issue. In that facility, cognitive problems, behavioral problems or both probably are measured or coded inaccurately.

The confidence limits and thresholds used in (B1), (B2), and (B3) can be dynamically adjusted to reflect the patient population in the facility being analyzed relative to the patient populations in the reference facilities. Furthermore, thresholds can be adjusted to reflect the tolerance of payers, regulators, researchers or other end users for various kinds of data integrity issues. This can be done for individual facilities, chains of facilities, associations, or geographical regions.

When the set of data fails to meet any of criteria B1–B3, that data set has a data integrity issue. The issue is a data validity problem unless the facility has unusual characteristics that explain each issue. If documentation of these characteristics is lacking, data may be regarded as lacking validity.

Data integrity for multiple assessments of the same patient—i.e., sets of longitudinal data, requires the following additional conditions:

C1) Repeated assessments follow a pre-specified schedule (i.e., the data from repeated assessments have the correct sequence of dates);

C2) Special unscheduled assessments are performed when required by the application of pre-specified rules (e.g., In the event of a significant change in clinical status and care needs, a complete MDS reassessment is required. Therefore, if a major change in care needs was noted between MDS #1 and MDS#2, either MDS #2 would be a full MDS, or a full MDS, #3, would be required within 14 days of MDS #2);

C3) Demographic variables and other fixed data are constant from one data vector to the next;

C4) Changes over time are consistent with the coded diagnoses, conditions, and prognosis. For example, a patient with Alzheimer's disease, impaired short-term memory and severely impaired decision-making on a given assessment would not be expected to have normal short-term memory and decision-making on his next assessment, unless the diagnosis had proved to be in error.

Conditions (C1), (C2), and (C3) should always be true; an assessment in which either one of them is not true has a data validity problem that may impact the data analysis. This implies an underlying problem with the process of assessment, coding, data entry and data transmission. If condition (C4) does not hold, there is a data integrity issue which usually but not always reflects a data validity problem.

In describing the features of the Data Integrity Audit System of the present invention, the following definitions are utilized:

"Data Integrity Audit" is henceforth abbreviated as "DIA".

"Prospective DIA" is synonymous with "Real-Time DIA"

"Real-Time" means immediately available, as in data provided back to a user immediately upon its computation by a computer.

"Locked" MDS records are those that no longer are subject to revision—whether or not they have been submitted for payment or regulatory review.

"Unlocked" MDS records are subject to modification before submission to payers or regulators. The term "unlocked" is synonymous with "modifiable".

"Clinical record" comprises the medical record, drug administration records, therapists' reports, and all similar documentation kept at a nursing facility. The clinical record offers contemporaneous information about the resident's health status and functional status, and about services rendered.

"CPS" means Cognitive Performance Scale. Cognitive Performance Scale is a measure of cognitive capacity derived from MDS items.

"Independent expert assessment" is a process carried out by a qualified expert in long-term care resident assessment, that comprises bedside examination of a resident, interviews with caregivers, and review of the clinical record, followed by a determination of how the expert would score the set of MDS items that are the subject of the assessment.

"Nursing facility" and "nursing home" are used interchangeably. Throughout this application, in paragraphs not specifically referencing individual MDS items, "facility" or "nursing facility" may be replaced by "healthcare provider" or "service provider," and "MDS" may be replaced by "standardized assessment tool."

"Clinical documentation" may be replaced by "independent documentation."

"Unusual clinical circumstances" or "special clinical circumstances" may be replaced by "special or unusual circumstances."

Similar obvious substitutions apply to describe the application of the methodology outside the healthcare domain.

The Data Integrity Audit system has two versions: i) The Prospective ("Real-Time") Version and ii) The Retrospective Version. The primary purpose of the prospective version is to check individual patients' assessment data before they are added to a database or are used for the purpose of care planning, reimbursement, utilization review, etc. Clinicians and other evaluators are to use the results of the Prospective Data Integrity Audit either to correct errors or to improve documentation in the clinical record. The data submitted for a Prospective Data Integrity Audit are "unlocked"—i.e., subject to correction or revision rather than "locked" by the order of payers or regulators. (The Prospective Data Integrity Audit can be applied to locked data as well. If it generates recommendations for clinical record documentation, the documentation can be added retrospectively. If significant errors are found on the MDS, regulations require that a new MDS be completed and submitted that incorporates the correction.)

The purpose of the Retrospective Version is to aid the clinical and administrative staff of the care provider organization in care planning, program evaluation, staff education, setting of priorities, estimation of contingent liabilities from data validity problems, etc. Specifically, it offers perspectives on processes of assessment, coding, and documentation that could be producing invalid data. It gives advice for improving data integrity in specific areas of weakness. It estimates the financial impact of data validity problems on the provider organization. Within provider networks and chains, it can help management identify clinical and administrative strengths and weaknesses, identify and disseminate best practices in assessment and documentation, and estimate the overall financial impact of data validity problems. Regulators and payers can use the Retrospective DIA to identify individual MDS-based payment claims that should not be paid prior to a review of clinical documentation. In addition, they can use it to identify facilities that produce grossly invalid or potentially fraudulent MDS assessments.

The system of the invention provides for "feed-forward" between the Retrospective DIA and the Prospective DIA. If a Retrospective DIA for a specific provider or group of providers shows an excessive rate of a specific item response or combination or item responses, the Prospective DIA can be customized for that provider or group so that it will produce a notice to the user every time that problematic item or combination is encountered. The notice will remind a user that their facility's rate lies beyond confidence limits, so that any additional instances of that item or combination will require especially careful documentation. In other words, the specific items or combinations are viewed as facility-specific or group-specific data integrity issues. They would become data validity problems when the documentation in the clinical record did not adequately support them.

One embodiment of the Prospective Data Integrity Audit is as a service available to nursing facilities online. Facilities using the system make a secure connection to a special Web site, using any Web browser equipped with software adequate to meet security requirements. They then transmit unlocked data from each patient assessment, using the same protocol for electronic data interchange they use in transmitting data to State agencies. The client facility receives a list of the data integrity issues found, along with likely causes, suggested fixes, and prompts for documentation of issues that might represent unusual clinical circumstances rather than errors in assessment or coding.

As a function of processing Prospective Data Integrity Audits, the firm operating the server would have access to fresh data on every patient admitted to every client facility. With the client's permission, this information could be used to target clinical and commercial messages to the clients. The timing and content of the messages is determined by the data coming in about patients' clinical status, payer, expected stay, and service needs. Suppliers of goods and services to nursing facilities are likely to pay to get their messages to facility decision-makers exactly when the facility is likely to need their products. For example, if several newly admitted patients are incontinent of urine, the facility may have need of additional incontinence supplies. A vendor of such supplies would be able to get a message to the facility administrator that referred to the recent admissions and their needs. The client facility would be able to choose whether to be identified to vendors as the recipient of their messages. If client facilities wished to remain anonymous, vendors still could still be told the number and characteristics of the facilities that received their message.

The system also permits client facilities to aggregate their demand for goods and services, permitting it to function as a "virtual purchasing group." The data flowing to the server supports statistically sound predictions of the need for services and supplies, and also indicates when those services or supplies will be needed, and by what facilities. This enables the facilities in the virtual purchasing group to lower their vendors' costs, and therefore permits the facility group to negotiate better prices.

Elements of the Automated Data integrity Auditing System include the following:

1) The operational definition of data integrity given above.
2) A specific set of data integrity tests.
   a) Individual-level tests: Individual item responses, or combinations of item responses, that are missing, violate coding rules, are done on incorrect dates, are logically impossible, are clinically improbable, or require special documentation.
   b) Group-level tests: Ratios of item responses or item response combinations in which the numerator and denominator define a logical relationship among MDS items, or the rate of a specific item response or combination. Or, other statistics calculated from facility level MDS data, such as internal consistency estimates or correlation coefficients. These are compared with a test-specific threshold level determined by empirical study of facility-level data, or set by reference to regulatory policy, payer policy, or experience with audits. When the ratio or other statistic is beyond the threshold, there is a data integrity issue. The issue becomes a data validity problem when the clinical record does not have adequate documentation to explain the observed ratio or statistic.
   c) Obvious tests: Tests of data completeness and timeliness, adherence to coding conventions, and logical consistency.
   d) Non-obvious tests: Tests that reflect clinical insight, that are validated by empirical studies of large samples of facility-level data. (Example: It is not logically necessary that a resident with severely impaired decision-making cannot establish their own goals, but clinically this is true, and the relationship has-been validated on a sample of over 200 facilities.)
   e) The method of:
      i) combining test data to develop an assessment of overall data integrity;
      ii) describing the probable process problems giving rise to data integrity problems;
      iii) providing suggested fixes to data integrity issues when these are not obvious;
      iv) providing specific data integrity tests based on clinical or statistical considerations, as opposed to coding conventions, completeness, assessment dates, or logical relationships.
   f) A set of specific data integrity tests.
   g) A set of process analyses and recommendations linked to each data integrity test.
3) A system of weights and thresholds. The system assigns a vector of ordinal variables, binary variables, and a threshold percentage to each data integrity test. The elements of the vector are as follows:
   a) An ordinal variable representing the relevance of the items involved in the data integrity test to measuring quality of care. For example: a relevance weight of three may represent items that are involved in calculation of an official quality indicator; a relevance weight of two, items that are involved in calculation of a performance measure used by the facility but not mandated by payers or regulators; a relevance weight of one, items that are involved in calculation of risk factors for a quality indicator or performance measure; and a relevance weight of 0, items that are not involved in either risk factors or outcomes for quality indicators or performance measures used by the facility or its payers or regulators.
   b) A binary variable representing the relevance of the items involved in the data integrity test to the calculation of reimbursement. Multiple binary variables may be used to represent multiple payment systems.
   c) An ordinal variable related to the estimated likelihood that a documentation audit or regulatory scrutiny will be triggered by the data integrity issue identified by the test. For example: A predictive weight of three may represent a likelihood of audit greater than or equal to 50%; a predictive weight of two, a likelihood of audit between 10% and 50%; a predictive weight of one, a likelihood of audit greater than zero but less than 10%; and a predictive weight of zero, that the item is not used by auditors or regulators. These variables can be updated periodically based on the actual experience of a facility, a chain, or the facilities in a geographic region.
   d) A threshold value for failure of the test at the facility level. This will be a number between zero and one that defines a threshold for the failure of a test at the facility level. In the case of data integrity tests applicable to individual assessments, the number is the proportion of instances for the given data integrity test that are failed. In the case of statistical data integrity tests applied only to aggregated data, such as internal consistency statistics or correlation coefficients, the threshold is a value of the given statistic. Considering a large population of discrete nursing facilities, many data integrity tests show a bimodal distribution, with one mode at or near 100%, and another several points lower. Multiple threshold values can be used to characterize the severity of an issue.
   e) A "frequently failed" binary variable that equals one when the data integrity test is failed by a relatively high proportion of facilities with generally valid data. "Relatively high proportion" means greater than or equal to 10% of facilities, but for items with no exceptions expected "relatively high proportion" may be defined to mean greater than or equal to 5% of facilities.

f) The "inexcusability weight": an ordinal variable representing how likely it is that there is a clinically reasonable explanation of the data integrity issue at hand. For example, gross logical contradictions, incomplete assessments, and missed deadlines have no excuse. On the other hand, typical clinical relationships among MDS items may not apply in a specialized clinical population. For example: an inexcusability weight of two signifies that there is no reasonable explanation; an inexcusability weight of one signifies that there may be a valid explanation in a special population or under unusual clinical circumstances; and an inexcusability weight of zero signifies that there are many valid explanations for the failure of the data integrity test related to specific clinical circumstances.

4) For each data integrity issue, a description of likely reasons for its existence—including errors in assessment, coding, data entry, or interpretation of MDS items.

5) For each individual data integrity issue identified by the DIA, a recommended strategy for resolving the issue. This can involve changing one or more item responses, ensuring adequate documentation in the clinical record, or both.

6) For each facility-level, chain-level, association-level or community-level data integrity issue, a description of usual causes and suggestions for addressing them at the organizational level. This may involve changes in work processes, education and training, or information systems.

7) Benchmarking an organization's incidence of data integrity issues against a reference sample of similar organizations (i.e., facilities, chains, associations, or communities). Benchmarks and aggregated scores are used in reporting the data integrity performance of multi-facility organizations.

a) Creation of a "report card" organized by sections of the MDS. The report card is a matrix of scores; the vertical axis lists MDS sections; the horizontal axis lists perspectives, e.g., Quality, Medicare Reimbursement, Medicaid Reimbursement, and Regulatory Compliance. Scores are given in each "subject" (MDS section). The scores for each "subject" (MDS section) are based on patient-level data integrity tests that involve items in that MDS section. Each such test yields a percentage—the proportion of patients who passed that data integrity test. Each of the section scores is based upon: a percentage of data integrity tests passed, where each test is weighted based on the perspective (quality, reimbursement, or regulatory), the excuse score, and the likelihood of failure of the test by facilities with generally valid data. The specific formulas are presented below.

b) Presenting scores as (graphical) percentile ranks within a reference sample of facilities or organizations, highlighting the one that is the subject of the report, is used to characterize the DIA performance relative to the benchmarks.

8) A listing of patients with data integrity issues, organized by room number in the facility. For each patient, a medical record number, the MDS sections involved, the DIA tests involved, the date of the assessment, the principal diagnosis, and the type of assessment are given. This permits a rapid determination of the locus of assessment errors, and helps target process improvement and in-service training.

9) Comparison of "report cards" across facilities in a chain or association. This permits the identification of strengths and weaknesses among the facilities vis-a-vis resident assessment with the MDS. This in turn aids in performance evaluations of administrators and MDS coordinators, and the planning of in-service training and process improvement efforts.

10) Documentation prompts. Data integrity issues can arise from valid assessments of patients with unusual clinical features or circumstances. Likewise, facility-level data integrity issues can arise when facilities treat unusual clinical populations. However, quality monitors, payers, and regulators may nonetheless focus audits on providers with data integrity issues. Therefore, careful documentation of special circumstances is especially important for MDS items involved in failed data integrity tests. The Data Integrity Audit system provides immediate online prompts to check documentation and to ensure adequacy of documentation in such circumstances. It suggests potential reasons why a data integrity issue might arise from a valid assessment, and offers language that might be useful in writing the supporting documentation. For example, a data integrity issue arises when a patient is scored on the MDS as being comatose, yet also is scored on the same MDS assessment as having a problem with wandering. An unusual circumstance that would give rise to this issue on a valid MDS assessment is one where a patient is admitted to a facility in a coma, but then recovers and begins to wander in a state of confusion. The MDS refers to events occurring in a 7-day assessment reference period rather than reporting the state of affairs at one moment in time. If the 7-day assessment period captured the patient's awakening from coma, it could validly assess the patient as comatose and wandering. The Data Integrity Audit points this out, and suggests that the user carefully document the patient's emergence from coma during the assessment reference period.

Documentation prompts also are provided for data integrity issues specific to a particular setting—facility, chain, or community. These are issues that do not represent logical contradictions or clinical or statistical improbabilities, but nonetheless are items of special concern to payers or regulators. Special data integrity tests are added to the standard set to determine when these documentation prompts are needed. For example, a payer may determine that occupational therapy is used excessively in a particular nursing home chain, and therefore scrutinize the documentation of occupational therapy hours and indications and goals of the therapy. A data integrity test would be added that would be "failed" whenever occupational therapy hours exceeded a specified threshold. The "failure" would trigger a documentation prompt. Of course, the results of these tests would not be included in the calculation of data integrity scores described above. A separate section of the DIA report can be added that shows the number of documentation prompts by diagnosis, location within the facility, and sections of the MDS involved. As with other sections, this section can be used to guide facilities' process improvement efforts and information system design.

In one embodiment of the DIA, the provider of the DIA service systematically gathers information about payers' and regulators' audit criteria, and individual facilities' and chains' audit histories. In particular, the DIA service provided to a specific facility or chain includes data integrity tests and documentation prompts addressing the circumstances that have previously triggered focused medical reviews and audits, reduction or denial of payment, or citations by regulators. For a given facility, past experience may allow the computation of a rate at which each data integrity issue has been identified by a payer, regulator, or surveyor as a problem calling for action. Issues with nonzero rates receive maximum weights on the regulatory compliance dimension. For example, consider a facility that has had RUGS-based Medicare payments reduced because a high level of rehabilitation frequently was delivered to residents with severe cognitive impairment. More particularly, over the past six months, 30% of residents in this facility with severe cognitive impairment and 325 minutes of rehabilitation have had their RUGS payments reduced. That is, the data integrity issue has a 30% chance of being seen by the external authorities as a true data validity problem. The DIA for that facility would identify a data integrity issue when the MDS showed severe cognitive impairment (on the MDS-based Cognitive Performance Scale) and 325 minutes of rehabilitation in the past 7 days. This is a data integrity issue because severe cognitive impairment usually limits an individual's ability to profit from rehabilitation. The feedback to the facility would point out that specific clinical record notes were needed to explain the appropriateness of rehabilitation in this resident with severe cognitive improvement. The DIA user would be prompted to reassess cognitive performance, actual hours and days of rehabilitation, and review the clinical record documentation of both the therapy hours and their medical necessity. The test would receive a maximum weight on the regulatory compliance dimension. On the other hand, suppose a facility were audited on all cases with a high level of rehabilitation without regard to the remainder of the MDS. In this case, the data integrity test would trigger a documentation prompt but would not contribute to the data integrity scores.

Documentation prompts may be given for data integrity issues that describe clinical relationships that might appear improbable on a first look, but that have many potential explanations or "excuses." These issues receive no weight in the calculation of "report cards". However, such data integrity issues still can become data validity problems if the documentation in the clinical record is inadequate to explain them. The system prompts the user for appropriate documentation in these situations, suggesting where to find and where to record the necessary elements of documentation, and at times proposing specific language to express those elements. Documentation prompts based on a facility's Retrospective DIAs is a feature that facilitates staff training and clinical process improvement.

The Prospective DIA provides item change recommendations and documentation prompts. The latter are triggered by universal data integrity issues such as those described in this application, as well as specific issues triggered by regulators' concerns as expressed through publicly-available reports and transmittals, the aggregated regulatory and reimbursement experience of the facilities using the DIA system, and each facility's prior audit history. When specific issues are also universal issues that capture clinical relationships among MDS items, they are included in the data integrity scores and receive the highest weight on the regulatory compliance and/or reimbursement dimensions. When they are not universal issues or when they are merely specific payers' documentation requirements for individual MDS items, they are not included in the data integrity scores.

11) Estimation of the financial impact of data integrity issues. Payers for nursing home care, e.g., Medicare fiscal intermediaries (FIs), will decrease payment to nursing homes if their reviewer determines that some of the care rendered was not medically necessary, if the relevant MDS assessment was not filed on time, or if there were errors in assessment and coding of items critical to the calculation of the resident's Resource Utilization Group (RUG). Except for downgrades or denials of payment based on gross errors or failure to perform and file electronic MDS assessments on time, reimbursement reductions almost always are based on a lack of the documentation necessary to resolve a data integrity issue, or documentation insufficient to justify high-cost treatment of a resident with a clinical assessment not typical of those receiving that treatment.

To estimate the reimbursement impact of a data integrity issue, the system calculates the expected RUGS reimbursement for each patient in the facility. Multiple payment systems are often used within a facility; e.g. Medicare, Medicaid, HMO, private pay, etc. The following description uses the RUGS reimbursement system that is used by Medicare. The financial estimation method described can easily be modified by one skilled in the art to accommodate various payment systems as long as they are based on the MDS.

In the DIA, RUGS payments are calculated several ways, reflecting different hypotheses about the integrity of the MDS and its relationship with clinical documentation:

Baseline: Assume that all data integrity issues are explained by documentation, and that all MDS item responses are accepted as valid. RUGS reimbursement is based on MDS items "as is."

Adjusted according to a payer's Formula: All data integrity issues are assumed to be true data validity problems, to which the payer responds by dropping each resident with an MDS-related data integrity issue to a lower reimbursement category according to a fixed scheme set by the payer. (Such a scheme for Medicare RUGS payments was recently published in HCFA Transmittal A-99-20.)

Adjusted minimally in favor of the payer: All data integrity issues are assumed to be true data validity problems. The audit system adjusts the item responses going into the data integrity tests to eliminate the data integrity issues, and then recalculates Medicare RUGS-based reimbursement on the new, revised MDS produced by these adjustments. The adjustments are made in the direction of lesser illness severity, functional impairment, and service intensity. This adjustment is clinically the "smallest" change that will eliminate the data integrity issue. These adjustments usually but not always lead to lower reimbursement under the RUGS system. For example, if a patient is assessed as able to stand and to walk, but is rated as unable to get out of bed without assistance, the adjusted MDS rates the patient as able to get out of bed with cueing and supervision only, rather than with physical assistance. In another example, a patient receives 360 minutes a week of physical therapy despite having severe cognitive impairment. The adjusted MDS indicates that the patient receives 180 minutes a week of physical therapy.

Adjusted minimally in favor of the care provider: A similar method is used, but the adjustments are made in the direction of greater illness severity, functional impairment, or service intensity. The estimated RUGS reimbursement sometimes but not always would be higher when calculated on the adjusted MDS. Continuing the first example above, this adjusted MDS would describe the patient as unable to walk without assistance; the transfer item would not be re-scored. Continuing the second example, the cognitive status item would be re-scored to indicate moderate cognitive impairment, and the minutes of rehabilitation would be left unchanged. As an example where reimbursement might increase, consider a patient said to transfer without assistance but unable to move in bed. This scenario would change the transfer item to indicate the patient had as much trouble with transferring as with bed mobility. In this case, the resident's dependency level would be higher, and RUGS reimbursement usually would be higher, as well.

If there is more than one data integrity issue involving RUGS items, the process requires iteration. That is, Data Integrity Audit tests are given in a standard order. After each test, the MDS is modified if necessary to eliminate any data integrity issue. This is continued through the entire list of data integrity tests. Then, the tests are applied again, to verify that new data integrity issues were not created by the changes just made. This process is repeated if necessary.

For example, an original MDS assessment, assessment A, determines the baseline RUGS group—this we call $A^{base}$. The next payment estimate changes the resident's RUGS group according to a formula (either explicitly provided by a payer, or demonstrated over time by a payer) that reassigns residents from one group to another. In this case, a table of reassignments gives the adjusted RUGS group—this we call $A^{formula}$. The last payment estimates are made by calculating the RUGS groups and reimbursements on an adjusted MDS in which some items have been altered. Adjustment can occur in one of two ways (that we are concerned with). The first adjusted MDS changes RUGS-related item responses on the MDS in favor of the payer—this we will call $A^{minus}$. The other changes RUGS-related item responses on the MDS in favor of the facility—this we call $A^{plus}$. Item responses are changed to the minimum extent necessary. Additional adjustment scenarios occur when one item in the DIA test is a RUGS-related item and the other is not. In this situation, priority is given to the adjustments that will impact reimbursement. The RUGS-related item will be-changed, even if the necessary change in the non-RUGS item would appear to be smaller.

DIA tests may involve large groups of individual assessments. Analysis of a group assessment is required in order to test the data integrity of the prevalence of a particular diagnosis, condition, or treatment, or to calculate internal consistency statistics or correlation coefficients. (The limits themselves may be set based on statistical analysis of customers' data by the DIA service provider, or by communications from payers and their intermediaries.) In $A^{minus}$: if a patient has a diagnoses or condition that has excessive prevalence in the entire population, the diagnosis or condition is assumed to be valid for the purposes of calculating the RUG. When a scale (i.e. all 17 mood items viewed as a depression rating scale; all 5 behavioral symptoms viewed as a behavior problem rating scale) fails a test of internal consistency, all scale items in the adjusted MDS are scored as zero (not present). If the correlation coefficient between two MDS scales is outside of the acceptable range specified by the DIA test, $A^{minus}$ changes items on both scales so that all of them are scored as zero (symptom or sign not present). Changes are made sequentially, following a pre-specified order as follows: Data integrity tests relevant to RUGS reimbursement applied in the order that the earliest MDS item in them appears on the MDS. As each test is applied, items are adjusted as needed to eliminate data integrity issues. Then, non-RUGS related data integrity tests are performed in a similar order, with adjustments made as needed to eliminate data integrity issues. Then, non-RUGS items are changed if necessary. Once all are made, the DIA is run again to ensure that all issues have been eliminated.

The dollar payment per diem for each RUGS group is then obtained from the payer or an intermediary. Based on these rates, the total reimbursement is estimated for patients with the RUGS groups specified by the table of reassignments, $A^{formula}$. Then, it is calculated using the RUGS group on the original data set $A^{base}$, and the adjusted MDS data sets $A^{minus}$ and $A^{plus}$. An obvious calculation gives the amount at risk in an MDS audit, as well as the potential gain in reimbursement from rectifying data validity problems, if it were the case that facilities' data validity problems arose from under-coding residents' impairments, diagnoses, symptoms, and treatments. These numbers give upper and lower bounds on the change in reimbursement that might come from a facility's reviewing and correcting residents' assessments, coding, and documentation. An additional, more conservative estimate of potential payment downgrades can be made by adjusting item responses only for data integrity tests classified as having no excuse for failure.

When a facility uses the Prospective DIA, it will have produced a "before" and "after" MDS, with the latter having fewer data integrity issues, and having careful documentation to justify any remaining issues. The difference in calculated reimbursement between them (i.e., $D = MDS^{after} - MDS^{before}$) indicates whether the facility tends to over-code or under-code its residents' problems and service use. If $D > 0$, under-coding is a significant problem to be addressed by management. If $D < 0$, over-coding is likely to be a problem. Knowledge of these problems and their magnitude helps management choose foci for its internal quality improvement efforts. Patients with characteristics associated with high positive values of D should be a special focus of education, training and process improvements with the goal of gaining appropriate reimbursement. Patients with characteristics associated with high negative values of D should be one focus of facility programs to ensure compliance with Medicare program integrity regulations. In both cases, the MDS itself can be used to select the patients who should be the focus of process improvement.

The Data Integrity Audit can serve as the foundation of a multi-function network with clinical and commercial benefits. By improving the accuracy of MDS assessments and their supporting documentation in the clinical record, the Prospective DIA improves care planning and quality monitoring, and thereby improves quality of care and regulatory compliance. Reimbursement can increase or decrease, but the fairness of reimbursement improves, and the risk of retrospective denials of payment decreases, because the integrity of the MDS data is demonstrable.

Numerous other opportunities flow from the fact the DIA would be an integral part of facilities' daily clinical operations. Because every patient's MDS assessment is checked by the DIA system, the operator of a server providing the DIA has a complete picture of each client facility's resident population, and pattern of admissions.

This information about the facilities' resident populations and patterns of admissions forms permits pinpoint marketing communication to the participating facilities. For example, if it were known that several recent admissions required oxygen therapy, the operator of the DIA system might send a customized message to the administrator and nursing director of the facility, mentioning the recent admissions of patients requiring oxygen. The message might notify them of the services of several different vendors of oxygen and respiratory therapy equipment, and might have banner advertisements or hot links to those vendors' Web sites, or advertisements at the end. The operator of the DIA system can charge vendors marketing fees in exchange for advertising space or hot links. Messages can be sent selectively to facilities in need of respiratory therapy services, without necessarily disclosing the names of particular facilities to the vendors without those facilities' consent.

Another application of the information is to clinical referrals. The MDS data collected via the Prospective DIA system can be analyzed by the DIA operator to determine a facility's areas of clinical strength and weakness, and what diseases and conditions treated by the facility had the best clinical outcomes. Patients in need of a nursing home bed could be matched with a suitable facility using this information. Outcomes might be better because patients would go where they would be treated best.

The daily use of the Prospective DIA makes it an excellent vehicle for conveying care planning suggestions, and thereby disseminating best clinical practices. Once a patient's MDS data are corrected and/or documentation of unusual situations is ensured, the DIA system operator can determine diagnoses, conditions, and high-risk situations. Educational text triggered by those diagnoses, conditions, and/or risk factors can be transmitted electronically to the facility. The messages can have within them hot links to references for further information about the clinical issues at hand. For example, if an MDS submitted for a Data Integrity Audit showed poor nutritional status and immobility, the patient would be determined to be at high risk for pressure ulcers. If the assessment of poor nutritional status and immobility remained on the "locked" MDS that would be transmitted to the responsible State agency, the facility would receive an electronic message that the patient whose assessment was just locked had a high risk for skin ulcers. It would advise consideration of special care, including nutritional support and a turning and repositioning program. The report page would also offer a hot link to practice guidelines for the prevention of pressure ulcers.

Each data integrity criterion specified herein is embodied by a number of data integrity tests. At the level of the individual, a test is a logical or mathematical statement about the coded values of variables in the database (i.e., item responses, or "items"). In the examples that follow, "(+)" is synonymous with "is checked" and "(−)" is synonymous with "is not checked". Examples follow.

1. Example of a coding accuracy and completeness test: 0<="B4"<=3 Item B4 is not missing, and it takes on a value between 0 and 3
2. Example of a logical consistency test.: If B3e(+) then B3a(−), B3b(−), B3c(−), and B3d(−)—If item B3e (none of the above) is checked then none of items B3a, B3b, B3c, and B3d (the "above" items) are checked.
3. Example of a logical consistency test: If G1AeA=2 then G1AeB>=2 (If a resident received physical assistance with bed mobility, then at least one person helped the resident).
4. Example of a clinical consistency test: if B3e(+) then B2a=1 (if the resident cannot recall the season, the location of their room, staff names and faces, and that they are in a nursing home, then there is a short term memory problem).
5. Example of a test of adherence to regulations: AB1<= A3a <=(AB1+14 days). The reference date of the assessment (A3a) is within the first 14 days after the date of admission (AB1).
6. Example of a test of clinical reasonableness: {Total (I1q+)>=Total (I1u+) for period [4/1/99:6/30/99]}— The total number of patients with Alzheimer's disease is greater than or equal the total number with dementia other than Alzheimer's disease, considering all assessments done over the second quarter of 1999.
7. Example of a test of a relationship between diagnoses and conditions and symptoms: If I11(+) then J3e(+) or J3g(+). —If a patient has arthritis then the patient has some degree of joint pain, either in the hip (J3e) or in some other joint (J3g).
8. Another example of a test of a relationship between diagnoses and conditions and symptoms: If J11(+) then I1f(+) or I1dd(+) or I1hh(+) or I1ii(+) or I3 includes the ICD code of a respiratory, cardiac, psychiatric, or neuromuscular diagnosis.—If a patient complains of shortness of breath then that patient has either congestive heart failure (J11(+)), an anxiety disorder (I1dd (+)), asthma (I1hh(+)), emphysema/COPD (I1ii(+)), or some other specifically diagnosed respiratory, cardiac, psychiatric, or neuromuscular diagnosis.
9. An example of psychometric internal consistency of a scale made up of related MDS items: {Cronbach's+for {(all E11x)|4/1/99:6/30/99}>=0.6} Considering all assessments done in the second quarter of 1999, and viewing items E1a through E1p as a single scale, the alpha statistic for the scale is at least 0.6. (i.e., the mood scale "hangs together"—removing any given item E1x does not significantly alter the relative mood scores of a population of residents.) This condition would be violated if, for instance, several mood items were practically never coded as present.
10. An example of test of correlation among scales made up of related MDS items: The Kendall rank correlation statistic tau (□) for [E1a-p vs. F2a-g for dates 4/1/99:6/30/99]>=0.6. The depression scale and a scale measuring personal relationship problems are significantly correlated, as expected, considering all full assessments done in the $2^{nd}$ quarter of 1999.
11. An example of a test of the relationship between therapies and indications for them: If P1bcA>0 then one of G4aB through G4fB is >0, or J2>0.—If a patient receives physical therapy then the patient either has some loss of voluntary movement (G4xB>0 for x between a and f) or has some pain (J2>0).

12. An example of the consistency of therapy days and therapy hours: For each x between a and f, (P1bxA*15)>=P1 bxB. The number of minutes of each specific therapy received in a week is greater than or equal to 15 minutes times the number of days on which at least 15 minutes of that therapy was given.
13. An example of logical consistency across multiple assessments: If A5>1 on assessment date x and date y>date x, then A5>1 on assessment date y.—If a patient is coded as being married, separated, divorced or widowed on one assessment, then the patient is not coded as "never married" on any subsequent assessment.
14. Another example of logical consistency across multiple assessments: If I1q(+) and B4<=2 at assessment date x and B6=1 at assessment date y where y>x and there is no assessment date z such that x<z<y, then B4>=2 at assessment time y. If a patient has Alzheimer's disease with moderately or severely impaired cognitive impairment on assessment date x, and there is no improvement between that assessment and the subsequent assessment on assessment date y, then the patient shows moderately or severe cognitive impairment on date y.
15. Another example of clinical consistency across multiple assessments: If G9=1 on assessment date x and assessment date y>x and there is no assessment date z such that x<y<z, then for each item G1aA through G1jA, the score on date x is >=the score on date y. If a patient's function in activities of daily living (ADLs) has improved between the last assessment and the present one, the patient is less dependent in each and every ADL. (This is not required by logical consistency, because it is possible though unlikely that a resident would be so improved in some areas that it would mitigate worsening in others.)

An important feature of the DIA system comprises the production of triggered text, which is sent electronically to the user within seconds by the operator of the service, over the Internet or a private network. Text is matched to each of the DIA tests that a user's data fails. In the Retrospective DIA, the triggered text:

1) points out why the data appear inconsistent;
2) enumerates the special clinical situations in which a completely valid assessment would yield such data;
3) indicates what would need to be documented in the clinical record to establish that such a situation existed;
4) describes typical reasons why facilities produce that type of data inconsistency;
5) suggests how the facility might modify its assessment, coding, or documentation to eliminate data validity problems of the type detected by the Retrospective DIA test.

In the Prospective DIA, the triggered text explains items (1), (2) and (3) above at the level of the individual patient. The system suggests how the specific data integrity issue might be eliminated by either changing one of the item responses in the test, or by ensuring documentation of the special clinical situations described in (2). Sometimes, other MDS items not involved in the test permit determination of what the likely reason is for the data integrity issue. For example, there is a data integrity issue when a patient has arthritis (I11(+)) but no joint pain [J3e(−) and J3g(−)]. If the patient had severely impaired expression [C4(+)] and periods of restlessness or agitation [B5d>0 or E1n>0], the DIA text could be augmented to read:

"You have described this patient as having arthritis, yet as having no joint pain. However, the patient's communication is rarely or never understood. It is likely that the patient has pain, but is communicating it through behavior rather than through words or gestures. The patient shows restlessness or agitation. It may be useful to determine whether this behavior decreases when acetaminophen or another pain reliever is given. If it does, the patient should be coded as having pain."

Triggered text is provided for the data integrity tests for the Retrospective DIA and for the Prospective DIA. Some of the triggered text comprises original and novel analyses of the causes for data integrity issues, both at the organizational level and at the individual level. Also, logic is provided which relates other patient-level MDS items to specific text recommendations for resolving data integrity issues. Triggered text can be made more facility-specific by modifying the triggered text according to MDS items not involved in the data integrity test itself.

In a preferred embodiment, the Data Integrity Auditor a portion thereof is presented in the form of a spreadsheet, such as an Excel spreadsheet, wherein the data integrity issues are identified and triggered text for each data integrity issue is presented in a pop-up text box.

In order to audit the integrity of data reported by service organizations and the like to assure that the quality of products or services provided complies with particular standards, the present invention provides various elements that are described below. It is noted that the relevant standards may be mandated by a government agency, a customer, a certifying or accrediting organization, or the leadership of the service organization. The following elements are provided in accordance with the invention:

1) A detailed, precise definition of the concept of data integrity, which is used as a proxy for data validity. Data integrity issues at the individual patient level are combinations of item responses, individual assessments, or a series of assessments of the same individual that either violate explicit rules for completing and coding the assessment, are logically impossible, or are very unlikely to be simultaneously valid. Data validity problems at the individual patient level are data integrity issues that either: (1) involve coding errors, incompleteness, or logical impossibility, or (2) involve combinations of item responses that are unlikely and not explained by supporting documentation of specific clinical circumstances. Data integrity issues of groups of patients (e.g., residents of a particular facility, patients treated by a specific clinical team) are either: (1) data integrity issues for individual patients within the group, (2) proportions of patients with specific item responses or combinations of them that are clinically unlikely in the given group or the patient population of which it is a subset; (3) relative rates of item responses (e.g., rates of specific diagnoses) that are clinically unlikely; (4) statistics derived from MDS data with respect to which the given group is an outlier (in reference to a set of comparable groups). For example, an internal consistency statistic for the MDS mood scale might average 0.6 with a standard deviation of 0.03 in a group of 1000 facilities; a facility with an internal consistency statistic of 0.4 would be an outlier. This would imply a data integrity problem for the MDS mood scale in that facility. In addition to internal consistency statistics for individual scales, the data integrity audit includes lower bounds for correlation coefficients between MDS scales that have a well-established clinical relationship. The lower bounds on correlation coefficients are then validated on a suitable reference sample of data of known or presumed validity.

2) A set of tests for the integrity of data (e.g., MDS data), some applicable to individual assessments, and others applicable only to a set of many assessments from the same facility, and still others applicable to data sets with multiple assessments of the same person at different times. It will be apparent to those skilled in the art that similar tests can be described for a wide range of health status/health service data structures, and for data structures in non-health related service industries, including without limitation financial services, education, and the hospitality industry. The ability to perform automated data integrity audits is of particular value in industries subject to substantial regulation, in which the collection and transmission of standardized data are mandated and required for funding, licenses, permits, determination of tax liability, etc. In the examples provided herein, discussion of the nursing home situation should be viewed as representative, and not as a limitation on the scope of the inventive method. In particular, for "nursing facility" one can read "home care agency", "hospital", "health plan", "health care provider", "service provider", "vendor", etc. For "MDS" one can read "OASIS", "HEDIS (Health Employers' Data and Information Set")", "standardized health status and health service data set", "customer interview and questionnaire data", etc.

3) A method of weighting data integrity test results for a collection of individual assessments to obtain data integrity scores for the facility that generated them.

4) A system for using different sets of weights to embody the perspectives of different users of the data. Weights are assigned to embody the perspectives of various users of the data, e.g., in the illustrated case, payers, regulators, and those interested in quality of clinical care. (In other embodiments, these perspectives might represent the perspectives of different categories of customers for a particular service.) 5) Text, triggered by data integrity issues at the individual patient level, that:
Explains to the user the nature of the data integrity issue.
Describes common assessment or coding errors that might account for the given integrity issue.
Explains what clinical documentation would be needed to establish validity of the given assessment.
Describes approaches to reassessment, coding, and documentation that would enable the data integrity issue to be resolved (and thus not be a data validity problem.)

6) Text, triggered by data integrity issues at the group level, with the same general content and purpose as described in (5) above.

7) In one embodiment of the invention, this text is provided to users in a prospective, "Real-Time" process, enabling them to correct assessment errors and documentation deficiencies before submitting a final, "locked" assessment to a government agency or other payer or regulator. Text, triggered by data integrity issues for collections of assessments from the same facility, that:
Explains to the user the nature of the data integrity issue;
Explains common reasons for the occurrence of the issue;
Offers specific choices for the resolution of the data integrity issue. Different potential revisions of item responses are suggested, any of which would resolve the data integrity issue. Where applicable, documentation that would support the validity of the current assessment is described. In some cases, the text offers specific phraseology for the documentation.

Data integrity is an intrinsic property of a set of data, such as health care and health service data, which can be determined without independent re-assessment of patients, direct observation of service delivery, or scrutiny of documentation in the clinical record. Note, however, that the process of initially specifying data integrity tests relies upon analysis of prior MDS data, associated clinical documentation, as well as a review of clinical literature. Data integrity refers to the relationship among different elements in the data vector for an individual assessment, or within a data set of many assessments. Specifically, Data Integrity is a measure of the extent to which the data set exhibits the following properties:

1) Completeness: All necessary elements of the given data set contain data. No cells in the data matrix have missing data, except when required by pre-specified rules (skip patterns).

2) Compliance with coding rules: All data items are in the proper format and within pre-specified ranges. "None of the above" responses are positive only when all of the referenced item responses are negative.

3) Logical consistency: Logical implications are respected. For example, if a given database in a medical setting has a yes/no item for diabetic neuropathy and a yes/no item for diabetes, a yes answer to the former item requires a yes answer to the latter item.

4) Clinical consistency and plausibility: In a medical setting, combinations of item responses are compatible with the characteristics of actual patients. For example, it is true in general that quadriplegic people cannot walk independently. So, answering yes to yes/no items both on quadriplegia and on independent walking would be clinically inconsistent. However, it would not be logically inconsistent. It is conceivable, for example, that a quadriplegic person might be equipped with a powered limb prosthesis that permitted some form of walking. In a large data set, however, clinical consistency requires that almost all of the patients with quadriplegia not be independent in walking.

5) Agreement of diagnoses, conditions, and symptoms: In the nursing home resident population that is assessed using the MDS, the majority of individuals with a given diagnosis or condition have one or more of the symptoms that ordinarily accompany it. The majority of individuals in the given data set with a particular symptom have one or more of the diagnoses and conditions that ordinarily explain it. For each such test, there is a threshold (e.g. 50, 75% or 95%) of assessments must have the relationship; otherwise there is a data integrity issue. Actual threshold values vary based upon the diagnoses and conditions being analyzed.

6) Agreement of treatments and indications: If the given data set indicates that a person receives a particular treatment, it also indicates that the person has one or more of the symptoms, diagnoses, or conditions that are the usual reasons for that treatment. These properties are applicable to individual assessments. For some tests, failure of the test by an individual patient assessment directly implies a data integrity problem and not just a data integrity issue. For others, there is a data integrity issue if the proportion of individual assessments (in a group) that have the issue exceeds a threshold based on empirical study of comparable patient groups. Finally, there are cases in which clinical record documentation must be reviewed to determine whether there is data integrity problem.

7) Psychometric consistency: If the database contains multi-item scales, the internal consistency of those scales (e.g., Cronbach's alpha statistic), measured within the given data set, exceeds a pre-specified criterion. If there are several scales within the database that are known to be correlated with one another, the matrix of covariance for those scales, calculated on the given data set, lies within pre-specified limits (e.g., 99% confidence limits for a representative sample of comparable patient populations other patient groups, presuming a normal distribution.). For each data integrity item tested, when the covariance between two scales falls below a specified threshold, text is triggered for that item. The threshold is determined by analysis of the distribution of the covariance coefficients in a sufficiently large and representative group of facilities. For example, a correlation is expected between the cognitive patterns of residents (MDS Item B) and the mood and behavior of residents (MDS Item E). When the threshold covariance is exceeded for the scales established for these two items, text is triggered:

Cognition and Mood

In your resident population, there is less than the usual degree of association between cognitive impairment and mood problems. Such an association exists because people with dementia are predisposed to depression, and people with depression have impairment in memory and concentration because of their depression.

Average CPS>3 (average cognitive status moderately impaired or worse)

Among your residents cognitive impairment is common. In light of this, one explanation for the lack of association between cognitive impairment and depression is that symptoms of depression are under-diagnosed. This risks a loss of RUGS reimbursement. Another is that cognitive impairment is overestimated. If this were the case and clinical documentation did not support the degree of cognitive impairment claimed on the MDS, it could raise a reviewer's concern about excessive billing or "RUGS creep". In either case, a remedy is to test cognitive function and to screen for depression more formally. In the most cognitively impaired residents, mood should be evaluated by observation, with special efforts to solicit the observations of the family and of night and weekend staff.

Average CPS<3

Most of your residents have relatively little cognitive impairment. The lack of association between cognitive impairment and depression may be due to under-diagnosis of cognitive impairment, or over-diagnosis of depression. In the former case, residents may not get the RUGS reimbursement they deserve. In the latter, there may be cause for a reviewer to question the reimbursement, unless documentation of mood symptoms is particularly good. In either case, a remedy is to test cognitive function and to screen for depression more formally. In the most cognitively impaired residents, mood should be evaluated by observation, with special efforts to solicit the observations of the family and of night and weekend staff.

8) Agreement with population incidence and prevalence data: The prevalence and incidence of diagnoses, conditions, and symptoms, within the clinical population described by the given data set, lie within pre-specified limits. Those limits are based on well-established rates in comparable patient populations. Prevalence and incidence rates may be either absolute or relative. As an example of the latter, consider the relative proportion of patients with Alzheimer's disease with respect to the proportion of patients with non-Alzheimer dementia. Other examples are provided hereinafter.

9) Plausibility of rates of change: If the database contains comparable data elements from multiple time points, the rates of change of those elements, within the given data set, lie within pre-specified limits. The limits are based on what is known about the natural course of the relevant diseases, conditions, symptoms, and disabilities. Examples are provided hereinafter.

A given data set is said to "fail" a particular data integrity test if the number of individual data vectors showing a given inconsistency exceeds a pre-specified threshold, or if the aggregate consistency measures described in paragraphs 7–9 above are outside the pre-specified limits. For tests of logical consistency and coding completeness and accuracy, failure of the test by a single patient assessment represents a data integrity problem.

Valid data must have data integrity. On the other hand, the criteria for data integrity can be sufficiently rigorous to make it statistically unlikely that non-valid data will satisfy them. An exception must be made, of course, for data sets that have perfect integrity but no relation to the actual patients whom they are supposed to describe. A gross form of fraud, not necessarily detectable by a data integrity audit, is based on duplicating a data set of known integrity, and submitting it with the names of different patients.

In general, however, improvement in data integrity is highly likely to lead to improvement in data quality. Furthermore, in the absence of gross fraud, higher data integrity will further all of the purposes for which health status/health service databases are intended.

The present invention describes an automated system for evaluating and scoring the integrity of data, such as MDS data. The system's reports also explain integrity issues to users. For each specific data integrity issue, the invention instructs the user in how to determine whether that issue represents a data validity problem. If it represents a validity problem, the invention shows the user how to remedy it. If it does not represent a validity problem, the invention shows the user what documentation is necessary in the clinical record to establish data validity. Finally, the invention offers guidance in how to prevent errors and promote data integrity and validity.

It will be apparent to one skilled in the art that the system described can be applied to virtually any health status and health service database in which there are a substantial number of logical, clinical, and statistical relationships among elements. Such relationships exist in almost all databases large enough and complex enough to be useful for the above-described purposes of quality monitoring, care planning, and reimbursement. If a representative sample of facilities is available for developing benchmarks and confidence limits, data integrity tests can include group-level tests of the absolute and relative prevalence and incidence of particular diseases, conditions, symptoms, and treatments. As noted above, the methodology is more broadly applicable to other types of services, as long as standardized assessments of individuals' characteristics and service use are performed.

A specific, preferred embodiment will now be described. It is noted that additional data integrity tests can be added in any of the nine categories of data integrity described. In the illustrated embodiment, only the first six categories of tests are implemented.

To calculate data integrity scores from a collection of individual tests of data integrity, scores must be combined in some way. This is done by using weighted sums of integrity test scores, where weights are based on the following factors:

The purpose for which the data set will be used. For example, if the data are to be used for reimbursement, items associated with the greatest incremental effect on reimbursement will receive the most weight.

The frequency with which the data integrity issue or problem occurs in data from facilities with generally valid data. Data integrity measures are benchmarked with respect to a large number of data sets from different data sources (e.g. different health care providers). Frequently "failed" data integrity tests receive less weight than those "passed" by a high proportion of the data sets evaluated.

The likelihood that the individual data integrity issue represents a validity problem that is, how likely there is a reasonable clinical explanation for an apparent inconsistency or lack of correlation. In assigning a weight based on this factor, logical inconsistencies will count more than an inter-scale correlation that exceeds usual limits. Thus, there is a "no excuse" factor, which is, e.g., either 0, 1, or 2. The no excuse factor depends on how serious the excuse for invalid data is. Thus, a 0 may be assigned as the no excuse factor when there are several plausible reasons why valid data might have the given issue; a 1 may be assigned when reasons exist for the given issue but are rare and unusual; and a 2 may be assigned when there is no excuse, as in the case of a logical inconsistency. The no excuse factor is used (e.g., by adding 1 to it and then using the sum as a multiplier) in order to weight the score of each data integrity test.

The basis of the weights assigned for each perspective will depend on an analysis of trends in the long-term care industry (or whatever other industry to which the method is applied), current government regulations and policies, and the expertise and knowledge of the user of the method. When the DIA is used within a chain or association, weights can be assigned on a customized basis to reflect the goals, concerns, preferences, and experience of the user. When the DIA is used within a network of facilities, tests can be added or removed on a periodic basis, or weights changed, to reflect changes in regulatory practice and the requirements of compliance programs.

DIA Score Calculation Formulas are used to combine the weights and DIA test results into a score. The formulas aggregate disparate, individual, stand-alone tests into a structured numeric result. This facilitates the interpretation of the collective impact on the user. In this application, this methodology is specific while being easily extended to quantify and characterize other organizational and business perspectives that may be important to the user. This approach can be extended to quantify other important characteristics as the clinical and business environment continues to change; this can be done by changing the weights and formulas to define a mathematical distribution that identifies and differentiates the "normal" organizations from the "outliers". The use of this approach is a fundamental component of the methodology described herein.

Example code for a score calculation formula is provided below:

The "Calculation Formulas" described below are examples of how the weights (described above) can be combined with DIA test results to quantify the impact on a dimension relevant to the user. In the example below, three business dimensions are shown: Clinical Quality, Risk Management, and Reimbursement. Cumulative points are calculated across all DIA tests. A score for each dimension is generated, which is then used to compare facilities against each other.

```
For Each DIA Test
{
    InexcusabilityWeight=1+
    DB.getfield("InexcusabilityWeight");
    FreqFailed=DB.getfield("FreqFailed");
    RUGS=DB.getfield("RUGSWeight");
    QofLife=DB.getfield("ClinicalQualityWeight");
    QI=DB.getfield("QIWeight");
    RUGSPaymentWeight=RUGS*InexcusabilityWeight;
    RUGSRUGSRegulatorWeight=((RUGS>0)+QI)*(1+
       InexcusabilityWeight–FreqFailed);
    ClinicalQualityWeight=1+((QI+QofLife)
       *InexcusabilityWeight)–FreqFailed;
    Threshold=DIAdata.getfield("FailurePoint");
    if (PercentageOfMDSsWithDIAissue >Threshold) then
       PaymentPointsOff+=PaymentWeight;
    RegulatorPointsOff +=RegulatorWeight;
    QualityPointsOff+=ClinicalQualityWeight;
End If
}
```

The FIGURE shows the flow of information in an implementation of the system for assessing nursing facilities ("NF"). At boxes 10 and 12 nursing facility residents and/or staff, respectively, complete a detailed resident assessment 14 such as the MDS described above. The data entered on the resident assessment forms is coded and entered as indicated at box 16 for representation as a "flat file" 20. This flat file is then formatted as indicated at box 62 for entry into the system database 64. At box 66, a coding and completeness check is conducted for each individual assessment to verify that the corresponding resident assessment data was properly coded and entered at the nursing facility (box 16). If so, the individual assessment is "passed", as indicated at box 68. However, if the individual assessment fails to meet the coding and entry requirements, as indicated at box 56, trigger text logic is applied (box 54) and a report is generated as indicated at box 52 to specify individual coding and completeness problems. The report, which is provided to the nursing facility, also suggests fixes for the specific problems identified.

Regardless of whether the individual assessment passes (box 68) or fails (box 56), the coded data will be passed to the database "DB" (box 58). If the individual assessment failed at box 56, indicators will be provided with the data passed to the database (box 58) to identify the bad fields in the data. The bad fields will not be used in any subsequent analysis of the data.

The good data are then analyzed. In particular, data integrity tests are applied by individual assessment, as indicated at box 42. Data integrity tests are also applied by aggregated assessments as indicated at box 44. The results of these tests are accumulated, as indicated at box 50, and further analyzed by applying trigger text logic on both and individual assessment basis (box 40) and an aggregated assessment basis (box 32). Weighting is also applied to the test results, as indicated at box 26.

In order to apply the weighting, various inputs may be used. For example, as indicated at box 60, data are provided pertaining to a cross section of participating nursing homes. Based on this data, industry trends are analyzed as indicated at box 48. This analysis is passed on to box 34, which uses the resulting information to assign weights to different tests. The weight assignment may also take into account various government policies and regulations, as indicated at box 36. Proprietary expertise and knowledge may also be factored into the weighting, as indicated at box 28. The weights assigned to each test are used in the analysis of the accumulated test results (box 50) as indicated at box 26. Then, data integrity scores are assigned to the test results from the various perspectives of interest.

After assigning the data integrity scores, a final report can be generated as indicated at box 22. This report includes the scores assigned to the resident assessment data integrity, and suggests any fixes necessary. The report includes results from the application of trigger text logic to the aggregated assessments (box 32) and the individual assessments (box 40). It should be noted that the individual triggered text is grouped by the type of data validity problem determined by the application of the trigger text logic (box 40), as indicated at box 30. The final report is provided to the nursing facility staff via mail, the Internet, telephone, communication network, or other suitable means. The report is used to educate the staff as to how the quality of the nursing facility and the reporting of resident assessment data can be improved, as indicated at box 18.

A real-time report can also be generated as to individual data integrity issues, as indicated at box 38. This report is based on the application of the trigger text logic to individual assessments at box 40. Such real-time reports, as well as the coding and completeness problem reports (box 52) are provided to the nursing facility staff for training and information purposes. As with the final report, these reports can advantageously be instantly delivered to the nursing facility via electronic means (i.e., in "real time").

It should now be appreciated that the present invention provides a vastly improved system for conducting, analyzing and grading assessments or the like based on data reported by a service organization. Reports are generated to advise the service organization of its "scores" in various areas of interest. The reports also explain data integrity issues to users. For each specific data integrity issue, the report instructs the user in how to determine whether that issue represents a validity problem and how to fix such problems. If a validity problem does not exist (but requires documentation), the report assists the user in obtaining documentation to establish data validity. Guidance is also provided in preventing errors and promoting data validity (and consequently data integrity). Advantageously, the data presented in the reports can be weighed according to different perspectives, depending on the interests of the user.

Although the invention has been described in connection with a specific embodiment thereof, it should be appreciated that numerous adaptations and modifications can be made thereto without departing from the scope of the accompanying claims.

What is claimed is:

1. An automated computerized method for evaluating and scoring the integrity of data provided by an organization, comprising the steps of:

receiving coded data from the organization;

checking the coded data for proper coding and completeness;

storing the coded data in a computer database together with indicators specifying bad data found during said checking step;

applying at least one data integrity test to a portion of data stored in said database that does not have any bad data specified by an indicator;

identifying any data validity problems located by said at least one data integrity test; and assigning a score to the portion of data based on said at least one data integrity test, said score being based upon at least one of (i) a percentage of data integrity tests passed, (ii) available explanations for any improbable data, and (iii) the likelihood of failure of a particular test; and generating a real-time report identifying at least one of (i) said score (ii) said data validity problems; or (iii) suggestions for resolving said data validity problems; wherein said report comprises at least one of: identification of data integrity issues; options for prevention of data validity problems which include the revision of individual item responses in the data provided and suggested documentation required to explain each data integrity issue that represents unusual clinical circumstances rather than an assessment error; identification of potential sources of assessment error and potential remedies for said assessment error; documentation prompts related to at least one of facility-level, chain-level, association-level, and community-level data integrity issues; and identification of in-service training and process needs.

2. A method in accordance with claim 1, further comprising: analyzing aggregate consistency measures with respect to a pre-specified limit.

3. A method in accordance with claim 1, further comprising:

generating a second report that identifies coding and completeness problems identified during said checking step.

4. A method in accordance with claim 3, wherein said second report also provides suggestions for resolving said coding and completeness problems.

5. A method in accordance with claim 4, further comprising:

generating a third report that identifies individual data integrity issues determined during the data integrity test; and providing said third report to said organization on a real-time basis.

6. A method in accordance with claim 5, wherein said third report also provides suggestions for resolving said data integrity issues.

7. A method in accordance with claim 1 further comprising:

applying weights to the results of said data integrity test; and using said weights to present said score from different perspectives.

8. A method in accordance with claim 7, wherein the weights applied to the results of the data integrity test are based on the likelihood of a plausible excuse for particular data.

9. A method in accordance with claim 1, wherein said report further comprises documentation prompts where the entry of valid data results in the generation of a data integrity issue, said documentation prompts indicating documentation to be checked and the required documentation needed to explain the data integrity issue.

10. A method in accordance with claim 1, wherein said report further comprises identification of common sources of error and identification of systematic repairs to correct said errors.

11. A method in accordance with claim 1, wherein the report further comprises identification of at least one of locations, dates, and assessment types giving rise to data integrity issues.

12. A method in accordance with claim 1, wherein said report further comprises identification of facility-level data integrity issues.

13. A method in accordance with claim 1, wherein said report further comprises identification of chain-level data integrity issues.

14. A method in accordance with claim 1, wherein said report further comprises identification of network-level data integrity issues.

15. A method in accordance with claim 1, wherein said report further comprises identification of community-level data integrity issues.

16. A method in accordance with claim 1, wherein the report further comprises:
   identification of specific areas of weakness based on repeated data integrity issues, including at least one of processes of assessment, coding, and documentation;
   identification of methods of improving data integrity issues in such area(s) of weakness; and
   identification of the financial impact of data validity problems on the provider organization.

17. A method in accordance with claim 16, wherein the report further comprises:
   identification and dissemination of best practices in assessment and documentation in response to common data validity issues.

18. A method in accordance with claim 16, wherein the report further comprises a notice that a facility's excessive rate of a specific item response or combination of specific item responses exceeds a predetermined confidence limit.

19. A method in accordance with claim 16, wherein the report further identifies specific patient populations for the purpose of determining education required at the point of service.

20. A method in accordance with claim 16, wherein the report further identifies specific patient populations for the purpose of determining specific sales channels of goods required by such a patient population.

21. A method in accordance with claim 16, wherein the report further identifies specific patient populations for the purpose of determining a patient referral network.

22. A method in accordance with claim 16, wherein the report further comprises identification of supplies needed by a facility based on the patient population of the facility.

23. A method in accordance with claim 1, wherein the data integrity test is based in part on the prevalence and incidence rates of diagnoses, conditions, and symptoms within a clinical population.

24. A method in accordance with claim 23 where the prevalence and incidence rates are absolute.

25. A method in accordance with claim 23 where the prevalence and incidence rates are relative.

26. A method in accordance with claim 1, wherein said data are provided via at least one of manual data entry or scanning of forms.

27. A method in accordance with claim 1, wherein at least one of said at least one data integrity test comprises testing for a logically consistent relationship between at least two items of said coded data.

28. A method in accordance with claim 1, wherein at least one of said at least one data integrity test comprises testing for a clinically consistent relationship between at least two items of said coded data.

* * * * *